US009084751B2

(12) United States Patent
Alderberth et al.

(10) Patent No.: US 9,084,751 B2
(45) Date of Patent: Jul. 21, 2015

(54) PREVENTION OF ALLERGY IN CHILDREN

(75) Inventors: Ingegerd Alderberth, Gothenburg (SE); Anna Rudin, Gothenburg (SE); Agnes E. Wold, Molndal (SE)

(73) Assignee: SWECURE AB, Stockolm (SE)

( * ) Notice: Subject to any disclaimer, the term of this patent is extended or adjusted under 35 U.S.C. 154(b) by 0 days.

(21) Appl. No.: 12/478,326

(22) Filed: Jun. 4, 2009

(65) Prior Publication Data
US 2009/0285858 A1 Nov. 19, 2009

Related U.S. Application Data

(60) Division of application No. 11/623,424, filed on Jan. 16, 2007, now abandoned, which is a continuation of application No. PCT/SE2005/001109, filed on Jul. 5, 2005.

(30) Foreign Application Priority Data

Jul. 16, 2004 (SE) ...................................... 0401876

(51) Int. Cl.
*A61K 39/085* (2006.01)
*A61K 39/00* (2006.01)
(52) U.S. Cl.
CPC ......... *A61K 39/085* (2013.01); *A61K 2039/541* (2013.01); *A61K 2039/542* (2013.01); *A61K 2039/543* (2013.01); *A61K 2039/55* (2013.01)
(58) Field of Classification Search
None
See application file for complete search history.

(56) References Cited

U.S. PATENT DOCUMENTS

| 6,692,746 B1 | 2/2004 | Terman et al. |
| 2010/0227013 A1 | 9/2010 | Bauer et al. |

FOREIGN PATENT DOCUMENTS

| DE | 10240866 A | 3/2004 |
| EP | 1411977 B1 | 4/2004 |
| WO | 91/12818 A | 9/1991 |
| WO | 99/40935 A1 | 8/1999 |
| WO | 0149319 A1 | 7/2001 |
| WO | 2004/087915 A1 | 10/2004 |
| WO | 2005/023853 A1 | 3/2005 |

OTHER PUBLICATIONS

Renz et al., Eur. Respir. J. 19:158-171, 2002).*
Schauer et al (Pediatr Allergy Immunol, 10:241-248, 1999).*
Smart et al (Clin. Exp. Allergy, 32:1552-1557, 2002).*
Adkins et al (Journal of Immunology, 157:1343-1349, 1996).*
The Pig Site (Basic Pig Husbandry—The Weaner; retrieved from the web, 2014).*
Database WPI. Week 199727, Derwent Publications, Ltd., AN1997-294856, JP 09-110704A,(ZH Kagaku & Kessei Ryoho Kenkyusho) Apr. 28, 1970, Claim & Detailed Description.
Mahon, B.P. et al. "The Rational Design of Vaccine Adjuvants for Mucosal and Neonatal Immunization". Current Medicinal Chemistry, 2001 vol. 8, p. 1057-p. 1075, the abstract; p. 1059, right column, second paragraph; table 2; p. 1068 "Immunization of the neonate".
Database WPI. Week 200467, Derwent Publications Ltd., London, GB; Class B04, AN 2004-678607 & CN 15 09725 A (Xiethe Group Co Ltd Shenyang City) Jul. 7, 2004, Abstract.
Collins, L. Vincent et al. "Mucosal Tolerance to a Bacterial Superantigen Indicates a Novel Pathway to Prevent Toxic Shock", Infection and Immunity, May 2002, vol. 70, No. 5, p. 2282-p. 2287.
Grundstrom, Susanna et al. "Superantigen-Induced Regulatory T Cells Display Different Suppressive Functions in the Presence or Absence of Natural CD4+CD25+ Regulatory T Cells in Vivo 1." The Journal of Immunology, 2003, vol. 170, p. 5008-p. 5017.
Rudin, A. et al. "Staphlococcal Enterotoxin B and High Dose Phytohemagglutinin Induce a Th1-Skewed Response in Neonates Irrespective of Atopic Status at 2 Years of Age." Scandanavian Journal of Immunology, 2000, vol. 52, p. 39-p. 44.
Soos, Jeanne M. et al. "Treatment of PL/J mice with the superantigen, staphyloccal enterotoxin B, prevents development of experimental allergic encephalomyelitis" 1993, vol. 43, p. 39-p. 44.
Lindberg, Erika et al. "Long-time persistence of superantigen-producing *Staphylococcus aureus* strains in the intestinal microflora of healthy infants" Pediatric Research, vol. 48, No. 6, Dec. 2000, pp. 741-747.
Lonnqvist et al., "Neonatal exposure to staphylococcal superantigen improves induction of oral tolerance in a mouse model of airway allergy" Eur. Journal Immunol., 2009, pp. 447-456.
Karlsson et al., "Allergen-responsive CD4+CD25+ Regulatory T Cells in Children who Have Outgrown Cow's Milk Allergy" J. Exp. Med. vol. 199, No. 12, Jun. 21, 2004, pp. 1679-1688.
Hori et al., "Foxp3: a critical regulator of the development and function of regulatory T cells" Microbes and Infection, 2004 Elsevier, pp. 745-751.
Bach, "The Effect of Infections of Susceptibility to Autoimmune and Allergic Diseases" N. England Journal of Medicine, vol. 347. No. 12, Sep. 19, 2002, pp. 911-920.
Holt et al., "99th Dahlem Conference on Infection, Inflammation and Chronic Inflammatory Disorders: The role of infections in allergy: atopic asthma as a paradigm" 2001 British Society for Immunology, Clinical and Experimental Immunology, 160 pp. 22-26.
Lundell et al., "Increased levels of circulating soluble CD14 but not CD83 in infants are associated with early intestinal colonization with *Staphylococcus aureus*" Clinical and Experimental Allergy 37, 2007, pp. 62-71.
Lundell et al., "High circulating immunoglobulin A levels in infants associated with intestinal toxigenic *Staphylococcus aureus* and a lower frequency of eczema" Clinical and Experimental Allergy 39, 2009 Blackwell Publishing Ltd, pp. 662-670.

(Continued)

Primary Examiner — Patricia A Duffy
(74) Attorney, Agent, or Firm — Gesmer Updegrove LLP

(57) ABSTRACT

The present invention relates to a use of bacterial superantigens in the manufacture of a pharmaceutical composition for mucous membrane administration for the prevention of inflammatory disorders in newborn infants, such pharmaceutical compositions, as well as method for prevention of inflammatory disorders.

14 Claims, 15 Drawing Sheets

(56) References Cited

OTHER PUBLICATIONS

Leung et al., "Presence of IgE Antibodies to Staphylococcal Exotoxins on the Skin of Patients with Atopic Dermatitis" The American Society for Clinical Investigations, Inc., vol. 92, Sep. 1993, pp. 1374-1380.

Nilsson, Eskil et al., "Topical corticosteroids and *Staphylococcus aureus* in atopic dermatitis" Journal of American Academy of Dermatology, 1992, vol. 27, pp. 29-34.

Hauser et al., "*Staphylococcus aureus* Skin Colonization in Atopic Dermatitis Patients" Dermatologica 1985, 170: pp. 35-39.

Leyden et al., "*Staphylococcus aureus* in lesions of atopic dermatitis" British Journal of Dermatology, 1974, 90 pp. 525-530.

Wold, "The hygiene hypothesis revised: is the rising frequency of allergy due to changes in the intestinal flora?" Allergy 1998: vol. 53(Supp. 46) pp. 20-25.

Smith et al., "Asthma and allergic rhinitis in adoptees and their adoptive parents" Annals of Allergy, Asthma & Immunology, Aug. 1998, vol. 81, pp. 135-139.

Emenius et al. "Building characteristics, indoor air quality and recurring wheezing in very young children (BAMSE)." Idoor Air, vol. 14, pp. 34-42, Feb. 2004.

Ronmark et al. "Four-year incidence of allergic sensitization among schoolchildren in a community where allergy to cat and dog dominates sensitization: Report from the Obstructive Lung Disease in Northern Sweden Study Group." J Allerggy Clin Immunol, vol. 112, No. 4, pp. 747-754, Oct. 2003.

Halmerbauer et al. "Study on the Prevention of Allergy in Children in Europe (SPACE): Allergic sensitization in children at 1 year of age in a controlled trial of allergen avoidance from birth." Pediatric Allergy and Immunology, vol. 13, Suppl. 15, pp. 47-54, 2002.

Arshad et al. "Primary prevention of asthma and atopy during childhood by allergen avoidance in infancy: a randomised controlled study." Thorax, vol. 58, pp. 489-493, Jun. 2003.

Kalliomaki et al. "Probiotics and prevention of atopic disease: 4-year follow-up of a randomised placebo-controlled trial." The Lancet, vol. 361, pp. 1869-1871, May 2003.

Kalliomaki et al. "Probiotics in primary prevention of atopic disease: a randomised placebo-controlled trial." The Lancet, vol. 357, pp. 1076-1079, Apr. 2001.

Holt et al. "99th Dahlem Conference on Infection, Inflammation and Chronic Inflammatory Disorders: The role of infections in allergy: atopic asthma as a paradigm." Clinical & Experimental Immunology, vol. 160, pp. 22-26, 2010.

Bach, Jean-Francois. "The Effect of Infections on Susceptibility to Autoimmune and Allergic Diseases." New England Journal of Medicine, vol. 347, No. 12, pp. 911-920, Sep. 2002.

Shi et al. "T helper cell subclasses and clinical disease states." Current Opinion in Gastroenterology, vol. 18, pp. 711-716, Nov. 2002.

Akdis et al. "Immune Responses in Healthy and Allergic Individuals Are Characterized by a Fine Balance between Allergen-specific T Regulatory 1 and T Helper 2 Cells." Journal of Experimental Medicine, vol. 199, No. 11, pp. 1567-1575, Jun. 2004.

Sakaguchi, Shimon. Naturally Arising CD4+ Regulatory T Cells for Immunologic Self-tolerance and Negative Control of Immune Responses, Annu. Rev. Immunol., vol. 22, pp. 531-562, 2004.

Ling et al. "Relation of CD4+CD25+ regulatory T-cell suppression of allergen-driven T-cell activation to atopic status and expression of allergic disease." The Lancet, vol. 363, pp. 608-615, Feb. 2004.

Perez-Machado, et al. "Reduced transforming growth factor-β1-producing T cells in the duodenal mucosa of children with food allergy." Eur. J. Immunol., vol. 33, pp. 2307-2315, Aug. 2003.

Karlsson et al. "Allergen-responsive CD4+CD25+ Regulatory T Cells in Children who Have Outgrown Cow's Milk Allergy." Journal of Experimental Medicine, vol. 199, No. 12, pp. 1679-1688, Jun. 2004.

Herrick et al., "To respond or not to respond: T cells in allergic asthma." Nature Reviews Immunology, vol. 3, pp. 1-8, May 2003.

Curotto et al. "The role of regulatory T cells in allergy." Springer Semin. Immun., vol. 25, pp. 295-310, Feb. 2004.

Cavani et al. "Human CD25+ Regulatory T Cells Maintain Immune Tolerance to Nickel in Healthy, Nonallergic Individuals." Journal of Immunology, vol. 171, pp. 5760-5768, Dec. 2003.

Akbari et al. "Role of regulatory T cells in allergy and asthma." Current Opinion in Immunology, vol. 15, pp. 627-633, Dec. 2003.

Nelson, Harold. "Advances in upper airway diseases and allergen immunotherapy." Journal of Allergy and Clinical Immunology, vol. 113, pp. 635-642, Apr. 2004.

Corry et al. "Interleukin 4, but Not Interleukin 5 or Eosinophils, Is Required in a Murine Model of Acute Airway Hyperreactivity." Journal of Experimental Medicine, vol. 183, pp. 109-117, Jan. 1996.

Bishop et al. "CC Chemokine Ligand 1 Promotes Recruitment of Eosinophils But That Th2 Cells During the Development of Allergic Airways Disease." Journal of Immunology, vol. 170, pp. 4810-4817, 2003.

Gonzalo et al. "Eosinophil Recruitment to the Lung in a Murine Model of Allergic Inflammation." Journal of Clinical Investigation, vol. 98, No. 10, pp. 2332-2345, Nov. 1996.

Mattes et al. "Intrinsic Defect in T Cell Production of Interleukin (IL)-13 in the Absence of Both IL-5 and Eotaxin Precludes the Development of Eosinophilia and Airways Hyperreactivity in Experimental Asthma." Journal of Experimental Medicine, vol. 195, No. 11, pp. 1433-1444, Jun. 2002.

Kanehiro et al. "Inhibition of Phosphodiesterase 4 Attenuates Airway Hyperresponsiveness and Airway Inflammation in a Model of Secondary Allergen Challenge." American Journal of Respiratory and Critical Care Medicine, vol. 163, pp. 173-184, 2001.

Henderson et al. "A Small Molecule Inhibitor of Redox-Regulated NF-κb and Activator Protein-1 Transcription Blocks Allergic Airway Inflammation in a Mouse Asthma Model." Journal of Immunology, vol. 169, pp. 5294-5299, 2002.

Oh et al. "Tryptase Inhibition Blocks Airway Inflammation in a Mouse Asthma Model." Journal of Immunology, vol. 168, pp. 1992-2000, 2002.

Henderson et al. "A Role for Cysteinyl Leukotrienes in Airway Remodeling in a Mouse Asthma Model." American Journal of Respiratory and Critical Care Medicine, vol. 165, pp. 108-116, 2002.

Finotto et al. "Treatment of Allergic Airway Inflammation and Hyperresponsiveness by Antisense-induced Local Blockade of GATA-3 Expression." Journal of Experimental Medicine, vol. 193, No. 11, pp. 1247-1260, Jun. 2001.

Cohn, Lauren. "Food for Thought: Can Immunological Tolerance Be Induced to Treat Asthma?" American Journal of Respiratory Cell and Molecular Biology, vol. 24, pp. 509-512, 2001.

Russo et al. "Suppression of Asthma-like Responses in Different Mouse Strains by Oral Tolerance." American Journal of Respiratory Cell and Molecular Biology, vol. 24, pp. 518-526, 2001.

Russo et al. "Prevention of lung eosinophilic inflammation by oral tolerance." Immunology Letters, vol. 61, pp. 15-23, 1998.

Nakao et al. "High-dose oral tolerance prevents antigen-induced eosinophil recruitment into the mouse airways." International Immunology, vol. 10, No. 4, pp. 387-394, 1998.

Obach et al. "The Prediction of Human Pharmacokinetic Parameters from Preclinical and In Vitro Metabolism Data." Journal of Pharmacology and Experimental Therapeutics, vol. 283, No. 1, pp. 46-58, 1997.

Rowland et al. "Clinical Pharmacokinetics—Concepts and Applications." Philadelphia: Lippincott, Williams & Wilkins, pp. 53-65, 1995.

Evenson et al. "Estimation of human dose of staphylococcal enterotoxin A from a large outbreak of staphylococcal food poisoning involving chocolate milk." International Journal of Food Microbiology, vol. 7, pp. 311-316, 1988.

Taylor et al. "Emetic Action of Staphylococcal Enterotoxin A on Weanling Pigs." Infection and Immunity, vol. 36, No. 3, pp. 1263-1266, Jun. 1982.

Wright et al. "Induction of Emetic, Pyrexic, and Behavioral Effects of *Staphylococcus aureus* Enterotoxin B in the Ferret." Infection and Immunity, vol. 68, No. 4, pp. 2686-2389, Apr. 2000.

(56) References Cited

OTHER PUBLICATIONS

Hu et al. "Induction of Emetic Response to Staphylococcal Enterotoxins in the House Musk Shrew (*Suncus murinus*)." Infection and Immunity, vol. 71, No. 1, pp. 567-570, Jan. 2003.

Miron et al., "Staphylococcal enterotoxin A: a candidate for the amplification of physiological immunoregulatory responses in the gut" Microbiol. Immunol., 2010, vol. 54, pp. 769-777.

The Supplementary European Search Report issued in connection with corresponding EP Application No. EP13746533.2 mailed on Mar. 24, 2014.

The English translation of corresponding WO Publication No. 0149319, published on Jul. 12, 2001.

* cited by examiner

Birch allergen stimulated PBMC at 4 months of age

Birch allergen stimulated PBMC at 4 months of age

US 9,084,751 B2

PREVENTION OF ALLERGY IN CHILDREN

PRIORITY INFORMATION

The present application is a divisional application of U.S. patent application Ser. No. 11/623,424 filed on Jan. 16, 2006, which is a continuation of PCT Application No. PCT/SE2005/001109, filed on Jul. 5, 2005, and claims priority to Swedish Application No. SE 0401876-8, filed on Jul. 16, 2004, all of which are incorporated herein by reference in their entireties.

TECHNICAL FIELD

The invention refers to the use of a bacterial superantigen for administration onto the mucous membrane in newborn infants for the prevention of allergies, autoimmune and inflammatory disorders.

BACKGROUND OF THE INVENTION

A number of diseases are characterized by an exaggerated or untoward immune reactivity against harmless antigens. Such diseases include allergies, autoimmune diseases and inflammatory bowel diseases. Normally, immune responses to harmless antigens are suppressed, a mechanism called tolerance. Tolerance to specific antigens, either exogenous or endogenous, may be induced either by mucosal or systemic exposure.

Tolerance occurs because helper T-cells are deleted, paralyzed or suppressed by other T-cells, so called regulatory T-cells.

Allergies

Allergies are defined as enhanced immune reactivity to one or several harmless environmental antigens, so called allergens. In IgE-mediated allergies, the allergic individual mounts an IgE-antibody response to proteins in foodstuffs, pollens, animal dander, etc. The IgE antibodies are produced by plasma cells developed from B-cells with specificity for a certain allergen. To become an IgE-producing plasma cell, the B-cell must receive help from a T-cell which is specific towards the same allergen. Activation of the T-cell by an allergen leads to the production of cytokines which promotes maturation of the B-cell into a plasma cell that produces IgE. The cytokines IL-4 and IL-13 are especially important in this respect. The subset of T-cells that produce such cytokines and help B-cells to become IgE-producing plasma cells, are called "Th2 cells" (Th=T helper cell). They also commonly produce IL-5, a cytokine which promotes maturation of eosinophils in the bone marrow and activation of such eosinophils that arrive to the tissue where an allergic reaction takes place. Once IgE antibodies are formed, they attach to mast cells in the tissues, for example around blood vessels and in the respiratory and gastro-intestinal tracts. When the allergic individual is exposed to the allergen, e.g. via inhalation or ingestion, minute amounts of intact protein allergen is taken up into the circulation, reaches the mast cells and binds to the IgE antibodies. Hereby the mast cell becomes activated and secretes a range of mediators that trigger the allergic reaction leading to symptoms forming disease entities such as hay fever, asthma, urticaria, atopic eczema, food allergy and allergic anaphylaxis.

In young children, the dominant symptom is atopic eczema, manifested as an itchy rash, or food allergy with gastrointestinal symptoms. Later on, the same child may develop hay fever, i.e. an allergic reaction in the nasal mucosa, caused by IgE-mediated hypersensitivity to environmental antigens. Non-allergic individuals do not mount IgE antibody responses to common environmental antigens, or develop a transient and weak IgE response to food antigens which gradually disappears. The propensity to develop allergy is established in the first few years of life (even if the allergy may manifest itself much later), which has led to a number of measures in order to try to prevent allergy development in children. For example, exclusive breast-feeding and avoidance of exposure to allergens has been widely promoted for many years. However, these measures have been completely ineffective, in that only minute amounts of antigen is needed to trigger IgE production. Many infants may, in fact, develop allergies to egg and cow's milk proteins while being exclusively breast-fed. Furthermore, children from families who have avoided pets are no less allergic to cats and dogs than children who have grown up with such pets in the family.

Allergy is much more common in industrialized countries compared to developing countries, which also applies to autoimmune and inflammatory disorders. This has led to the speculation that exposure to microbes in early childhood affords proper maturation of the developing immune system. However, it is not known which types of microbes are important for this to occur. There is an endless variety of bacteria, viruses and parasites, some of which might be important in providing the right type of stimuli to the immune system, others which may be ineffective, or even increase the risk of developing hypersensitivity or inflammation. For example, the microflora of the gastro-intestinal tract consists of several hundred species, some which are aerobic, while most are obligate anaerobes. The colonizing bacteria can be both Gram-positive and Gram-negative which each differ greatly in cell wall structure and their effects on the immune system.

Yoghurts and other traditional fermented food products have been tried both as therapeutic and preventive agents against allergy. *Lactobacillus rhamnosus* GG was given to children with severe cow's milk allergy and was shown to ameliorate intestinal inflammation and eczema in these patients. Based on these positive effects, *Lactobacillus rhamnosus* GG was given to mothers during pregnancy and lactation, and to bottle-fed infants in their formula, as a means to prevent development of allergy in their children.

Indeed, children who were exposed to these lactobacilli had less eczema by two and four years of age compared to children who were not exposed to these bacteria. However, it is important to note that there was no reduction in IgE levels or allergy with respiratory symptoms in children who had been exposed to these lactobacilli during infancy (Kalliornàki et al. Lancet. 2001 Apr. 7; 357(9262):1076-9 and Kalliornàki et al. Lancet. 2003 May 31; 361(9372):1869-71).

*Staphylococcus aureus* Enterotoxins

Certain bacteria produce toxins, i.e. protein molecules with highly damaging potential. Most bacteria which produce toxins are pathogenic, i.e. cause disease. But toxin-producing bacteria may also reside in the normal flora of the respiratory and/or gastrointestinal tracts without causing harm. For example, newborn infants are commonly colonized by toxin-producing *Staphylococcus aureus* (*S. aureus*) in their intestines during their first year of life without showing any symptoms from this colonization. The toxins these strains produce: *S. aureus* enterotoxin A, B, C or D, or TSST-1 (toxic shock syndrome toxin-1) have so called superantigen function. Superantigens have a bifunctional binding capacity: they bind both to the major histocompatibility complex II (MHC II) molecule of an antigen-presenting cell and to the T-cell receptor. Whereas a normal antigen only binds to T-cells that have specificity towards just that antigen, the "superantigen" binds to all T-cells that share one certain δ-chain in their receptor, i.e. belongs to a certain V8-family. This means that they bind to and activate a large proportion (10-30%) of the T-cells in human beings or animals, resulting in a massive cytokine production that may lead to shock and severe symptoms, even death. This is the mechanism behind toxic shock syndrome caused by superabsorbent tampons. TSST-1 producing *S. aureus* may colonize the tampon, produce TSST-1 which is absorbed across the vaginal epithelium and cause shock. A method to prevent the development of superantigen-induced shock may be to expose mucosal surfaces to the particular superantigen prior to challenge, which leads to specific tolerance to that superantigen (but not other antigens). This desensitization has been attributed to production of IL-10 (Collins et al., Infection and Immunity, Vol. 79, No. 5, 2002).

Toxin-producing *S. aureus* have been implicated in the pathogenesis of eczema, because eczematous skin lesions are often colonized by *S. aureus*. It has, thus, been suggested that toxins elaborated by *S. aureus* can worsen the reaction by stimulating T-cells, leading to tissue damage.

However, this ability of superantigens to stimulate T-cells has been suggested as a therapeutic treatment of cancers, infectious and allergic diseases by the employment of the superantigen to activate specific immune responses (U.S. patent no 2001046501 to Howard et al.), and in W003002143 to Antonsson et al. engineered superantigens including staphylococcal enterotoxins and TSST-1 are used in treatment of various forms of cancer. In W09112818 to Lamb et al. superantigens are parenterally administered to reduce the immune response including T-cells in order to prevent or treat rejection reactions, autoimmune disease, allergic disease and harmful responses to infectious agents. The mechanism proposed is via deletion of T-cells or via induced energy of T-cells. However a treatment that results in anergy or deletion of T-cells would not be recommended as prevention for allergy in children since decreased T-cell function would lead to a poor defense against infections.

Regulatory T-Cells (Tregs)

It is believed that allergy, autoimmune and inflammatory disorders are prevented by so called regulatory T-cells (Treg). These cells suppress activation of helper T-cells and thereby down-regulate many types of immune responses. One population of regulatory T-cells, named $CD25^+$ Treg (or $CD4^+$ $CD25^+CTLA-4^{1.}$ T-cells) are CD4-positive T-cells that have a high density of CD25 on their surface with a certain molecule, CTLA-4, in their cytoplasm which functions in intracellular expression. $CD25^+$ Tregs have a capacity to down-regulate the expansion and activation of helper T-cells. Helper T-cells are T-cells which enhance immune responses such as T-cell mediated cytotoxicity, delayed type hypersensitivity and antibody production. Another marker that can be used to identify Tregs is messenger RNA for the gene Foxp3. Mice and humans which have a non-functioning Foxp3 gene develop a syndrome with high IgE levels in the blood, severe eczema, inflammation in the large bowel wall and autoimmune disease in several organs. This strongly suggests that a poor function of Tregs may cause several diseases characterized by untoward or unregulated immune and inflammatory responses: allergy, autoimmunity and inflammatory diseases.

Tregs are produced in the thymus and exit to the periphery in the first days of life in mice. In humans, cells of the Treg phenotype are present at birth, but express lower levels of Foxp3 compared with cells from adults. It has been described that the number and function of $CD25^+$ Treg can be increased by in vitro stimulation with polyclonal activators as well as specific antigens and transfer of these antigen-expanded cells into mice results in delayed development of autoimmune disease in susceptible mice. Repeated injection of the superantigen *Staphylococcus aureus* enterotoxin A (SEA) into v133- and V138 transgenic mice resulted in potentiated suppressive function of $CD25^+$ Treg as well as induction of suppressive function in CD25" T-cells (T-cells that do not express CD25 on their surface and which cannot suppress helper T-cell functions). Superantigen administrated in such a way also results in an activation followed by a severe reduction in the number of T-cells in the animal (GrundstrOm et al. Jour. of Immunology, 2003, 170, 5008-5017). This observed activation/reduction together with the fact that superantigen in the blood circulation leads to shock in humans are the main reasons why Staphylococcal enterotoxins administered into the blood are unsuitable for treatment of humans. Mice on the other hand are much more resistant to the adverse effects of superantigens.

Regulatory T-cells, so called Treg, have come into focus recently. As discussed above, Tregs have the ability to down-regulate many types of untoward immune responses, including allergy, autoimmunity and inflammatory bowel disease. Many methods have been designed to expand and activate this cell type in vitro with the purpose to transfer these expanded and activated cells back to the individual from whom they were derived. In this way, severe autoimmune reactions and transplantation rejections may, theoretically, be treated, as indicated from animal experiments. However, it is completely unethical and impossible to do such procedures as preventive measures in small children.

The present invention discloses a solution to this problem by activation of the immune system by mucosal exposure to *S. aureus* toxins having a superantigen function, in order to expand and activate regulatory T-cells in vivo in early infancy. By this pretreatment, these cells will already be active when the child becomes exposed to potential allergens in the food and environment. Production of IgE antibodies will be prevented and allergic diseases will not be produced in this child. The mucosal exposure ensures that no hazardous effects are produced. The health statuses of the infants included in this study have been thoroughly investigated by continuous registration of symptoms. The children who were colonized by superantigen-producing *S. aureus* did not exhibit more gastro-intestinal or other symptoms than other children and were, in fact, completely healthy.

As described above, *S. aureus* and its superantigen production has been regarded as detrimental in development of allergy and it has been suggested that *S. aureus* should be eradicated in atopic children.

SUMMARY OF THE PRESENT INVENTION

The present invention discloses a use of bacterial superantigens for the manufacture of a pharmaceutical composition intended for the administration onto a mucous membrane in newborn infants for the prevention of inflammatory disorders as defined below. Examples of superantigens include, but are not limited to the *Staphylococcus aureus* enterotoxins A, B, C, D, E or TSST-1 or derivatives thereof.

In one preferred embodiment of the invention the pharmaceutical composition is comprised of at least one of the *Staphylococcus aureus* enterotoxin producing strains.

In another preferred embodiment of the invention, the pharmaceutical composition comprising the superantigen is administered onto a mucous membrane, such as the intestinal or the nasal mucous membrane.

In another preferred embodiment of the invention, the pharmaceutical composition comprising the superantigen generates regulatory T-cells in vivo.

In a further preferred embodiment the pharmaceutical composition comprising the superantigen is administered to a newborn infant no later than 3 months after birth, more preferably no later than one week after birth, more preferably no later than 6 days after birth, more preferably no later than 5 days after birth, more preferably no later than 4 days after birth and most preferably no later than 3 days after birth.

In a further preferred embodiment the invention relates to a pharmaceutical composition, the composition being present as a liquid formulation.

In preferred embodiment thereof the composition is present as a liquid formulation provided with a gelling agent.

In an additional aspect of the invention, the use of the pharmaceutical composition comprising the bacterial superantigen provides a method for preventing allergy development, autoimmune and inflammatory disorders in children.

DETAILED DESCRIPTION OF THE PRESENT INVENTION

By the term "Inflammatory disorders or reactions" herein and in the accompanying claims is meant diseases caused by immune hyper-reactivity to endogenous or exogenous antigens comprising diseases such as allergies; e.g. food allergy, hay fever, asthma, urticaria, eczema, anaphylactic reactions; inflammatory diseases; e.g. ulcerative colitis, Mb Crohn; autoimmune diseases, e.g. type 1 diabetes, autoimmune gastritis, autoimmune thyreoiditis, autoimmune haemolytic anemia and thrombocytopenia, multiple sclerosis.

According to the present invention human infants who, very early in life, have been exposed to staphylococcal superantigen in vivo by colonization of their intestines by toxin-producing *S. aureus* (*S. aureus* enterotoxin A, B, C or D, or TSST-1), are less prone to develop gastro-intestinal symptoms from food allergy and possibly also eczema by 18 months of age than all other infants, including those who are colonized by non-toxin-producing *S. aureus* at the same site. In another aspect of the invention, human infants who are colonized by toxin-producing *S. aureus* in the first few weeks of life have more Tregs in their blood circulation by 4 months of age. Furthermore, their blood cells respond with less production of IL-5 and IL-13 than other infants in response to stimulation with birch pollen antigen, including those who are colonized by non-toxin-producing *S. aureus* at the same site. This suggests that they may have lesser risk of developing hypersensitivity and hay fever to birch pollen later in life. Also human infants who are colonized by toxin-producing *S. aureus* in the first few weeks of life have less T-cells with the surface marker CD29 in their blood circulation by 4 months of age. This suggests that they may have a lesser risk of developing inflammatory reactions.

As described above, *S. aureus* and its superantigen production has been regarded as detrimental in development of allergy and it has been suggested that *S. aureus* should be eradicated in atopic children. Thus it is indeed surprising that exposure to staphylococcal superantigen in vivo via colonization of the mucosal surfaces in the gastro-intestinal and/or respiratory tracts affords protection from atopy and eczema, since the general opinion is that it is harmful to be colonized by *S. aureus* and that their toxins could drive the immune system into an allergic response by their superantigen function.

Exposure to *S. aureus* toxins with superantigen function via injection into the blood circulation carries an unacceptable risk of side-effects. In contrast, we have found no increased occurrence of gastrointestinal or other side-effects in infants colonized in their intestines with toxin-producing *S. aureus* compared to non-colonized children.

The infants examined here were assessed for colonization of the gastro-intestinal tract by toxin-producing *S. aureus* by culture of a swab inserted into the rectum, or by culture of faecal samples. The presence of *S. aureus* in the gastrointestinal tract does not imply that the same infants may also carry the same *S. aureus* strain in their nasal cavity, in which case the toxins could exert their immune-regulating function by effects on the nasal mucosa. However, we have observed a similar colonization frequency of newborn infants in the gastro-intestinal tract and nasal cavity, and in many cases, the same strain was found at both sites and showed the same toxin-producing capacity.

A puzzling observation was that only very early colonization by toxin-producing *S. aureus* gave a significant protective effect. Although infants who did not develop allergy were persistently more often colonized by toxin-producing *S. aureus* than those who developed allergy, colonization which was initiated after the first week seemed to have little effect. This probably relates to either of two factors. Either the toxin is only produced in the intestines in very early life. Since *S. aureus* has only recently been recognized as an intestinal colonizer, it is not known whether the necessary conditions for toxin production are at hand in the infantile intestinal tract. Perhaps production of toxins requires the presence of oxygen. The intestinal milieu is quite rich in oxygen during the first days of life, but becomes more and more anaerobic once more different types of bacteria establish in the intestinal tract. Secondly, *S. aureus* decrease quite rapidly in population numbers after the first period of life, probably reflecting that they are not "professional" intestinal bacteria but can only reach substantial population numbers in the absence of a more complex intestinal flora. After some months *S. aureus* has decreased substantially and the amount of toxin produced may not be large enough to affect the immune system. A third factor may be that the intestinal mucosa is more permeable to *S. aureus* toxins in very early life. A fourth factor may be that once breast-feeding has been established, the antibodies in the mother's milk against *S. aureus* toxins reduce its chances to affect the infant's mucosa. Due to these factors a very early (within 7 days) colonization of *S. aureus* toxin-producing strains is probably essential. However, a direct administration of the bacterial superantigen onto the mucous membrane in appropriate doses may extend the time span for establishing the preventive effect up to the age of three months.

We have not noted any significant side-effects by colonization with toxin-producing *S. aureus* in infancy. In this study the parents recorded any gastrointestinal symptoms and diseases in the infants and there was no association between presence of toxin-producing *S. aureus* in the infant's intestines and such symptoms.

The present invention thus discloses that toxin-producing *S. aureus* by their strong T-cell-activating effects are able to induce expansion and/or maturation of regulatory T-cells that may later afford protection from allergy and possibly other diseases caused by untoward immune activation. Activation of the immune system by *S. aureus* toxins with superantigen function can be exploited to afford the natural immune activation of the infant's immune system that has been lost today due to our overly hygienic life-style.

BRIEF DESCRIPTION OF THE DRAWINGS

The following drawings form part of the present specification and are included to further demonstrate certain aspect of the present invention. The invention may be better understood by reference to one or more of these drawings in combination with the detailed description of the invention.

The following examples are included to demonstrate the preferred embodiments of the invention. It should be appreciated by those skilled in the art that the techniques disclosed in the examples which follow are given for the purpose of illustration only and are not intended to limit the scope of the invention.

Example 1

Characterization of CD25$^+$ Tregs

Figure 1A:
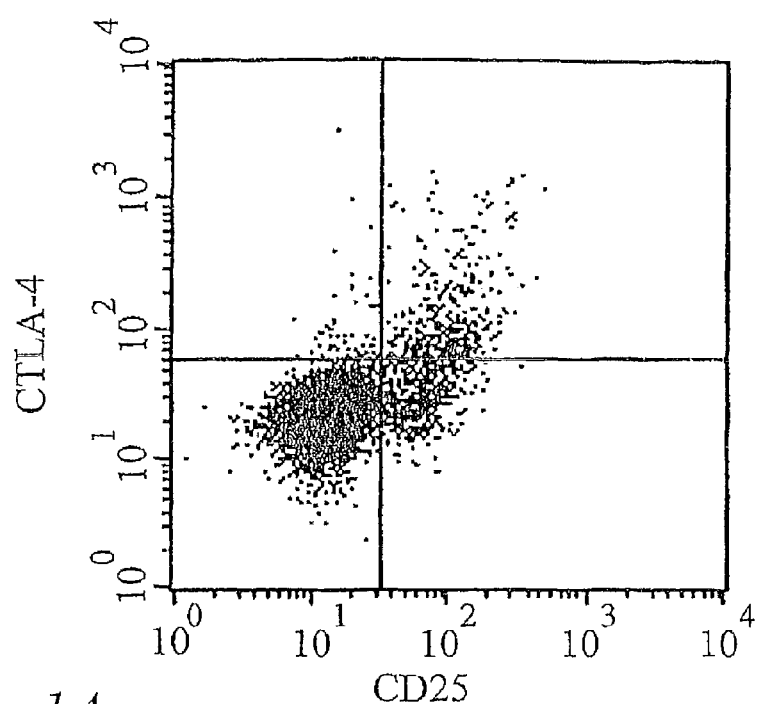
FIGS. 1 A-C show the characterization of CD25$^+$ Tregs by their expression of surface CD4 and CD25 and intracellular CTLA-4

The development of CD25$^+$ Tregs during the first 4 months of life were characterized by analysing the number of cells expressing surface CD4 and CD25 and intracellular CTLA-4 in peripheral blood obtained at 4 months of age compared to cord blood. FIG. 1A shows a dot plot of the expression of CD25 and CTLA-4 on gated CD4$^+$ T-cells. The cells in the upper right quadrant (A) were presumed to be CD25$^+$ Tregs.

Figure 1B:
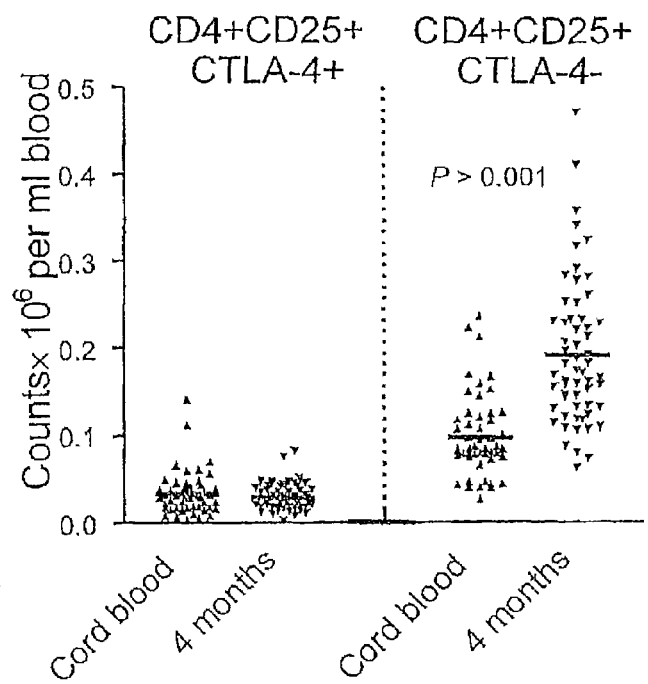

However, CD25 may also be upregulated on T-cells during activation, and whereas the average number of CD25$^+$ Tregs was similar in newborns and children 4 months of age, the number of CD4$^+$CD25$^+$CTLA-4$^-$ increased with age, indicating that they represented activated T-cells. This is seen in FIG. 1B, which shows the number of CD25$^+$ Tregs; CD4$^+$CD25$^+$CTLA-4$^+$ and CD4$^+$CD25$^+$CTLA-4$^-$ cells×10$^{-6}$ per ml blood, respectively, in newborns and children at 4 months of age. CD4$^+$CD25$^+$CTLA-4$^-$ cells are cells that recently have been activated, expressing CD25 on the surface, but without the intracellular expression of CTLA-4. These cells are however not able to suppress helper T-cell functions. The statistical significance refers to the difference between cord blood and 4 months (paired Student's t-test).

Figure 1C:
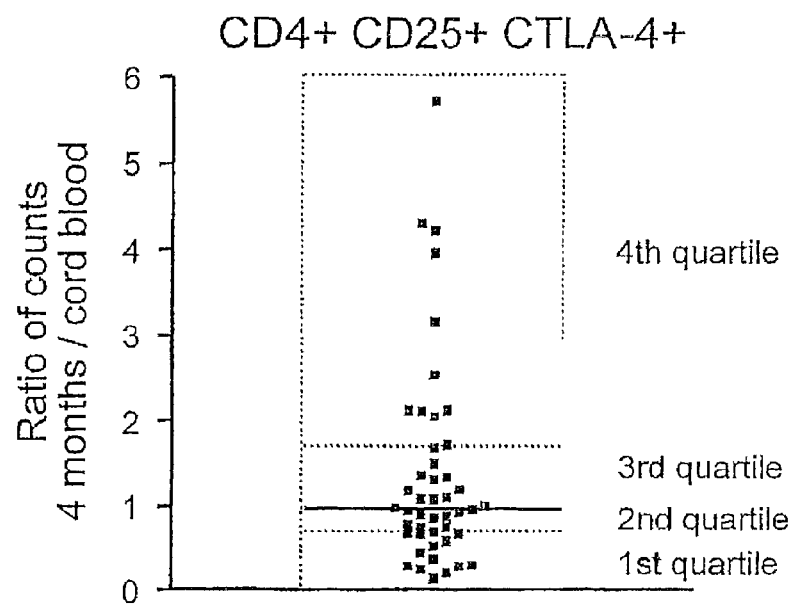

In order to study the development of CD25$^+$ Tregs (CD4$^+$CD25$^+$CTLA-4$^+$) in each individual child, we divided the number of CD25$^+$ Tregs at 4 months with the number of CD25$^+$ Tregs in cord blood and the ratios are shown in FIG. 1C. Interestingly, in some children the number of circulating CD25$^+$ Tregs increased 2 to 6-fold between birth and 4 months (ratio>1), whereas in others the count of these cells instead decreased (ratio<1). The children were divided into four quartiles depending on the expansion of CD25$^+$ Tregs in blood between 0 and 4 months of age (FIG. 1C).

Example 2

Figure 2A:
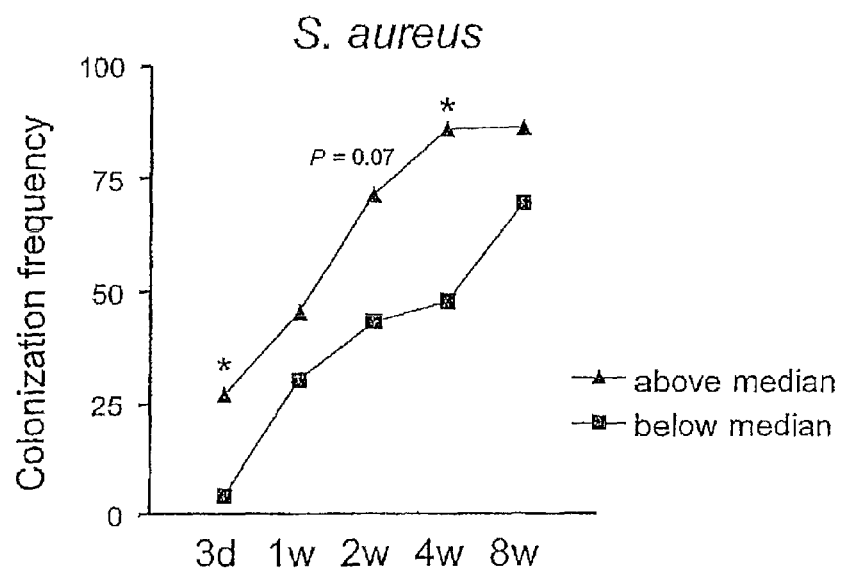
FIGS. 2 A-D show the type of colonization pattern in relation to the degree of Treg expansion FIGS. 3 A-C shows lack of effect of S. aureus activation of T-cells which are not regulatory.

Intestinal Colonization by Toxin-Producing S. aureus Induces Expansion of CD25$^+$ Tregs The type of colonization pattern was examined in relation to the degree of CD25$^+$ Treg expansion. FIG. 2A shows the frequency of colonization with S. aureus at 3 days, 1, 2, 4, and 8 weeks, in the groups of children above and below the median ratio of CD25$^+$ Tregs. We observed that the children who had a CD25$^+$ Treg ratio above the median were significantly more frequently colonized by S. aureus at 3 days and at 4 weeks than the children with a CD25$^+$ Treg ratio below the median. This was not observed for any other bacterial group or species (data not shown).

Figure 2B:
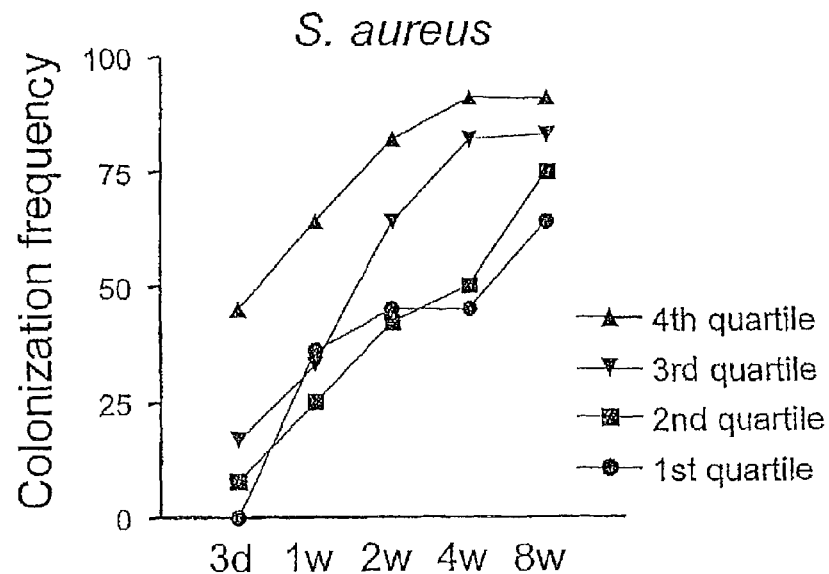

In FIG. 2B it is shown the S. aureus colonization pattern of infants belonging to each of the quartile with respect to CD25$^+$ Treg expansion. A 'dose-response' pattern was observed with the 4th quartile showing the most rapid acquisition. In this group, 45% of the children were colonized by S. aureus by day 3 and 91% by 4 weeks. None of the children with a CD25$^+$ Treg ratio in the 1st quartile were colonized by S. aureus by day 3 and only 45% by 4 weeks.

During the last decades, Staphylococcus aureus has become a common and persistent constituent of the intestinal microflora in Swedish infants. About 75% of the children born in the late 1990s had S. aureus in their stools at some point during their first year of life.

Figure 2C:
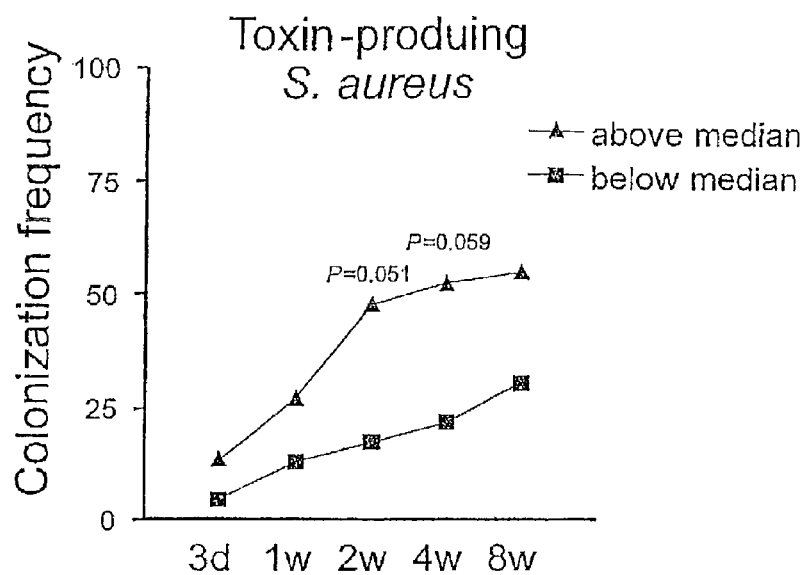
Figure 2D:
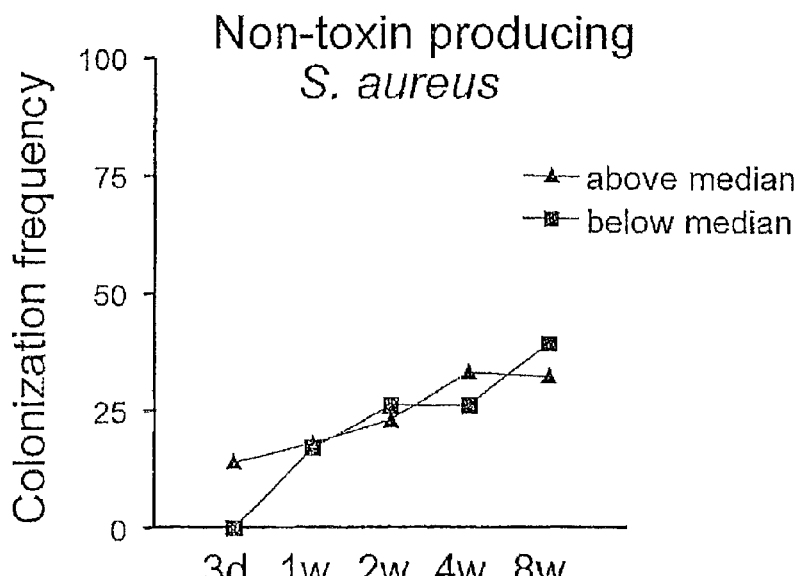

Almost 50% of the S. aureus strains residing in the gut of Swedish children produced at least one of the staphylococcal enterotoxins (SE) A, B, C or D or toxic shock syndrome toxin-1 (TSST-1), all with known superantigenic function. The question raised is if the expansion of CD25$^+$ Tregs in approximately half of the infants coincides with the colonization of superantigen-producing S. aureus? Strains of S. aureus were tested for their production of SEA, B, C, D and TSST-1 and divided into toxin- and non-toxin-producing strains. Interestingly, infants displaying CD25$^+$ Treg expansion above the median were more often (P<0.06 at 2 and 4 weeks) colonized by toxin-producing S. aureus (FIG. 2C). In contrast, colonization by non-toxin-producing S. aureus was almost identical with the infants whose CD25$^+$ Tregs expanded or decreased in proportion between birth and 4 months of age (FIG. 2D). The statistical significance refers to the difference between the frequency of S. aureus colonization between the groups of children above and below the median ratio. This suggests that intestinal colonization by superantigen-producing S. aureus in infants was responsible for the increase in CD25$^+$ Treg numbers in infants during their first 4 months of age.

Example 3

S. aureus Does Not Induce a General Activation of T-Cells

Figure 3A:
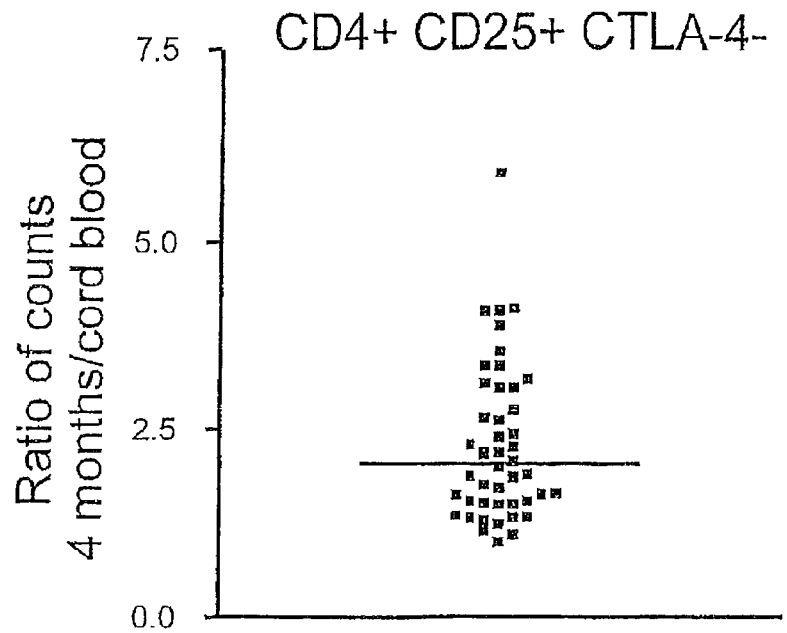

Apart from being a marker of CD25$^+$ Tregs, CD25 is also expressed by activated T-cells. FIG. 3A shows Ratio (4 months/cord blood) of number of CD4$^+$CD25$^+$CTLA-4$^-$ T-cells (cells that recently have been activated, expressing CD25 on the surface, but without the intracellular expression of CTLA-4. These cells are not able to suppress helper T-cell functions). In order to exclude that S. aureus induces activation of T-cells rather than generation of CD25$^+$ Tregs, the colonization frequency in children was compared with a ratio of the numbers of CD4$^+$CD25$^+$CTLA-4$^-$ T-cells above and below the median (2.03).

Figure 3B:
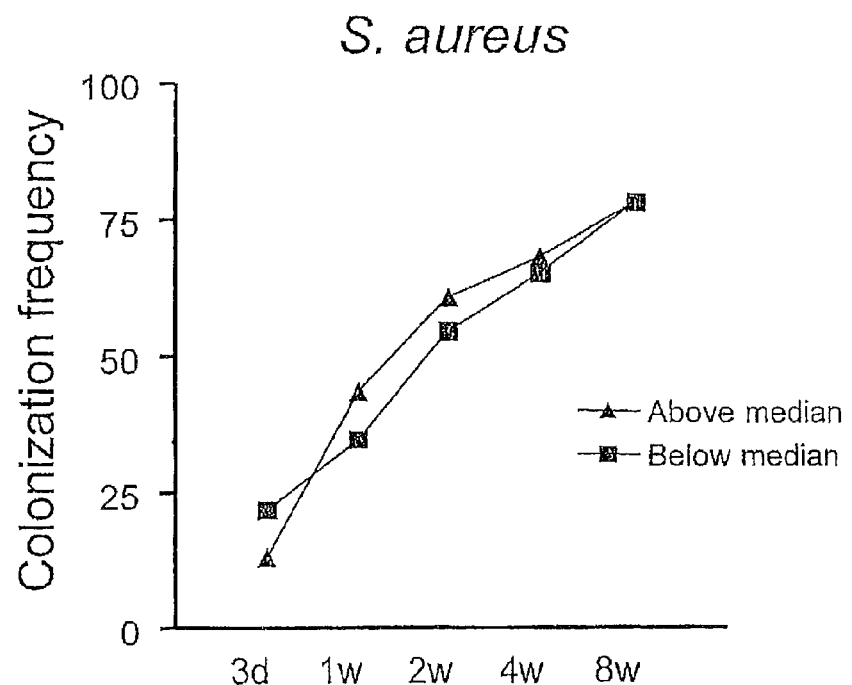
Figure 3C:
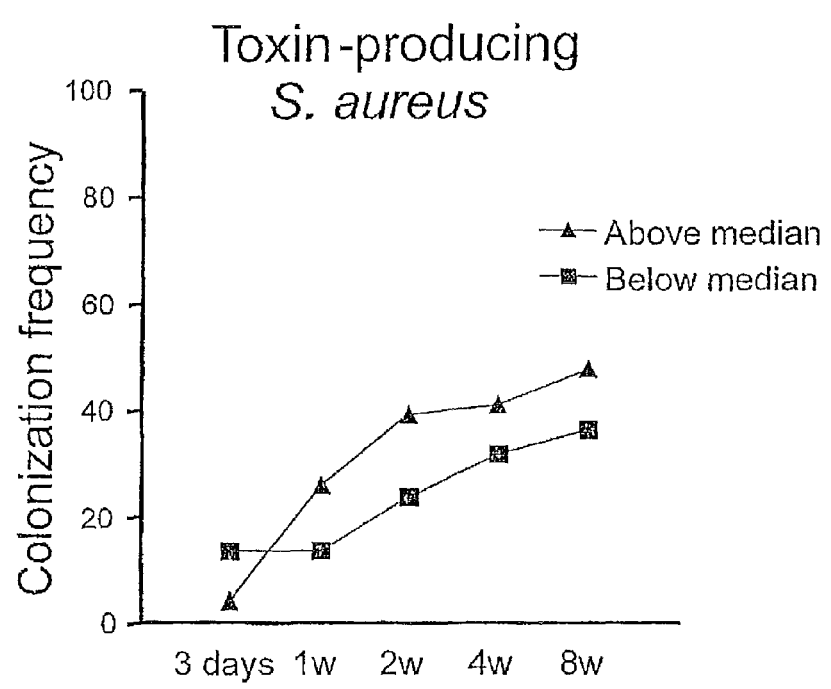

We observed no difference in *S. aureus* colonization between the groups of children at 3 days, 1, 2, 4, and 8 weeks, above and below the median, neither for total *S. aureus* (FIG. 3B) nor for toxin-producing *S. aureus* (FIG. 3C). These results support that toxin-producing *S. aureus* induce an increase in CD25$^+$ Treg counts and not only a general activation of T-cells.

Example 4

An Early Colonization by *S. aureus* is Important for the Expansion of CD25$^+$ Tregs The effectiveness of the specific time-point of colonization and introduction of CD25$^+$ Tregs was investigated. The CD25$^+$ Treg expansion from birth to 4 months of age was studied with respect to colonization with *S. aureus* at 3 days as well as 1, 2, 4 or 8 weeks.

Figure 4A:
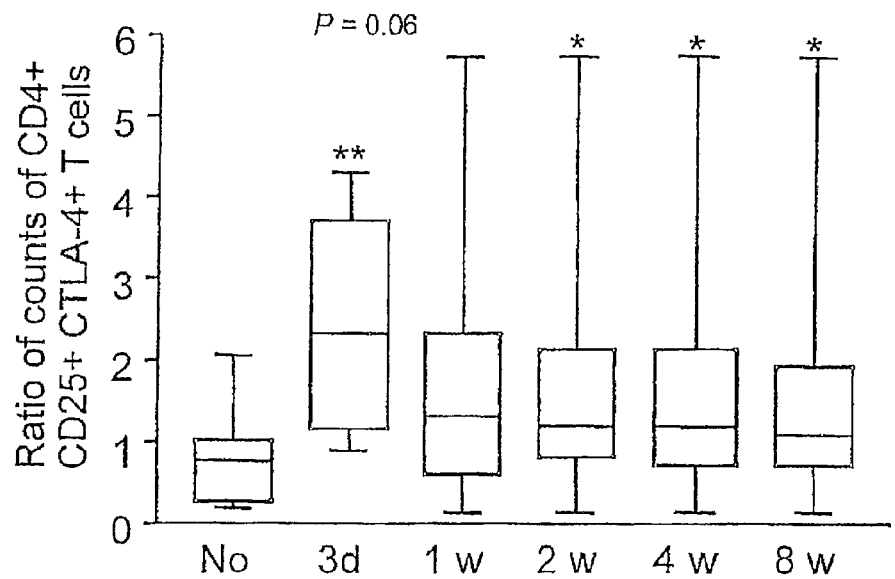
FIGS. 4 A-E show the importance for the time-point of S. aureus colonization and activation of Treg expansion.
Figure 4B:
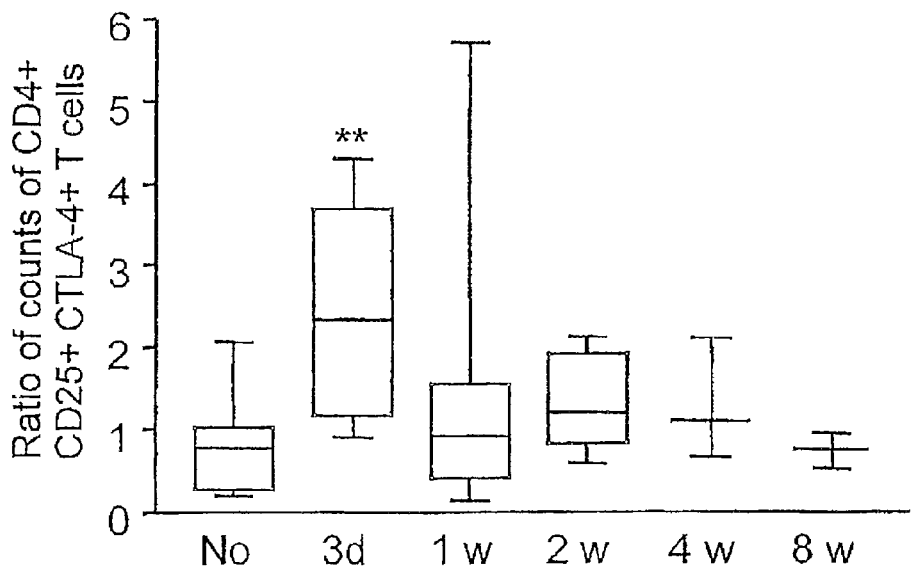

As shown in FIG. 4A, the children with intestinal *S. aureus* at each time-point during their first two months of life acquired a higher number of CD25$^+$ Tregs than the children who were not colonized by *S. aureus* during their first 2 months of life. It could be observed that the expansion of CD25$^+$ Treg was related to the time-point of appearance of *S. aureus* in the intestinal flora. Exclusively the children who were colonized as early as 3 days of age had a significant increase in their number of CD25$^+$ Tregs compared to the children who did not harbour *S. aureus* in their gut flora during their first 8 weeks of life (FIG. 4B). Similarly, acquisition of a toxin-producing *S. aureus* strain by day 3 was associated with a more pronounced increase of CD25$^+$ Tregs compared to infants never colonized with *S. aureus* (P<0.05, data not shown). Acquisition of non-toxin producing *S. aureus* was not associated with significant expansion of CD25$^+$ Tregs (data not shown).

Figure 4C:
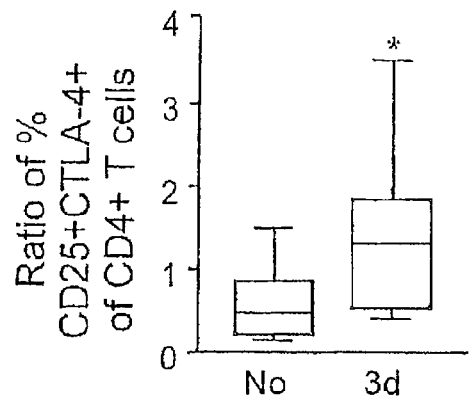
Figure 4D:
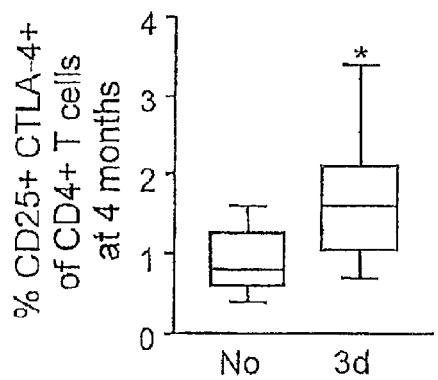
Figure 4E:
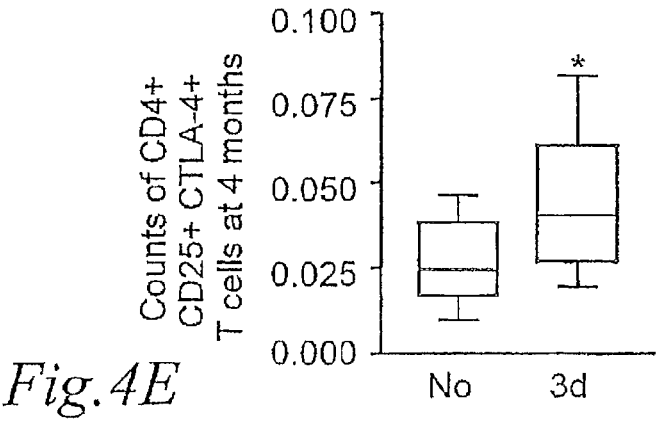

A significant relation between the colonization with *S. aureus* from day 3 and the expansion of the fraction of CD4$^+$ T-cells expressing CD25 and CTLA-4 (FIG. 4C) as well as the fraction (FIG. 4D) and absolute number ($\times 10^{-8}$ per ml blood) (FIG. 4E) of these cells at 4 months of age in children colonized with *S. aureus* at 3 days of life compared to children who were not colonized with *S. aureus*. The statistical significance refers to the difference between the children with intestinal colonization with *S. aureus* at the various time points and the children who were not colonized with *S. aureus* at any time during the first 8 weeks of life (No), *P<0.05 and **P<0.01 (Mann-Whitney U test).

Altogether, this suggests that appropriate stimulation of the immune system during the very first days of life or a long-term exposure is of importance for the induction of CD25$^+$ Tregs.

Example 5

Figure 5A:
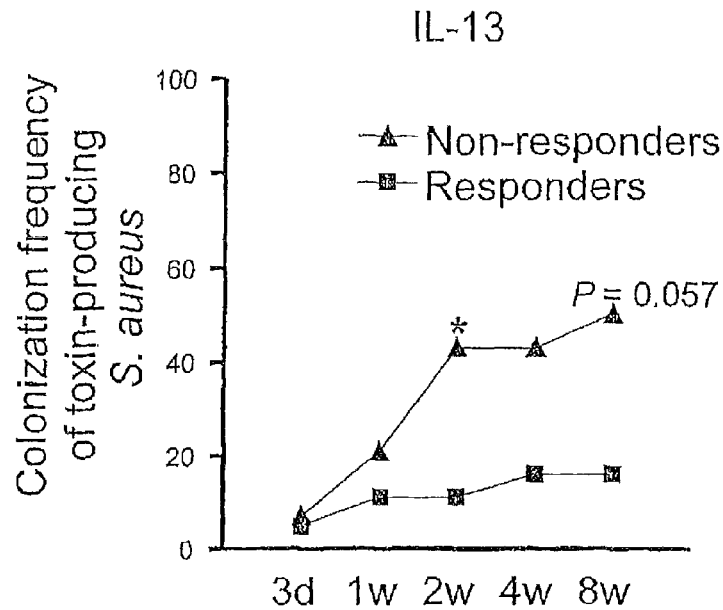
FIGS. 5 A-F shows the prevention of responses to birch allergen by early colonization with toxin-producing S. aureus.
Figure 5B:
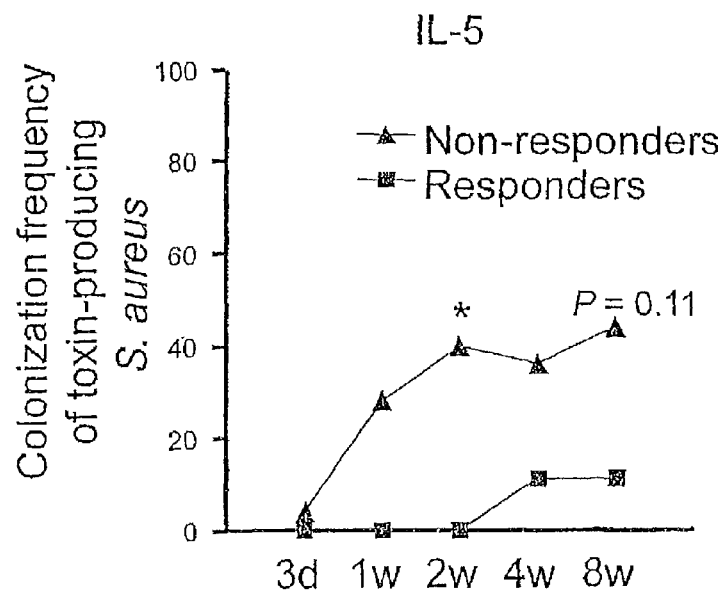
Figure 5C:
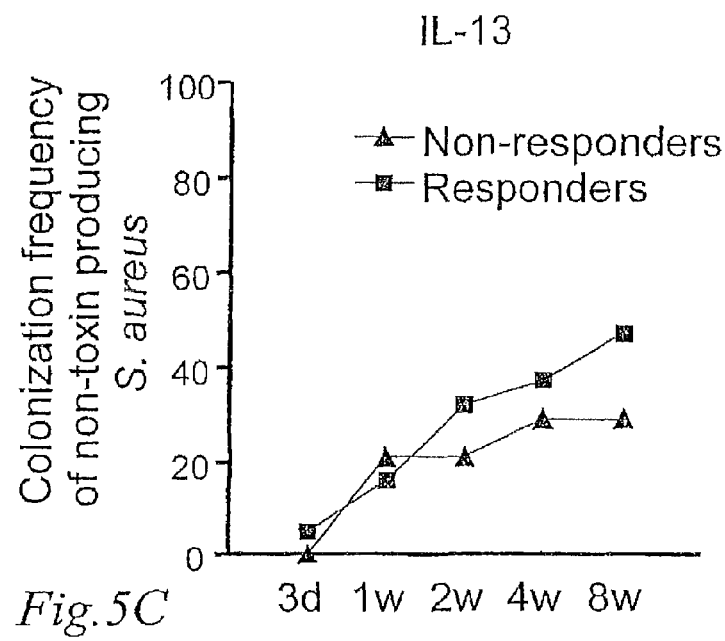
Figure 5D:
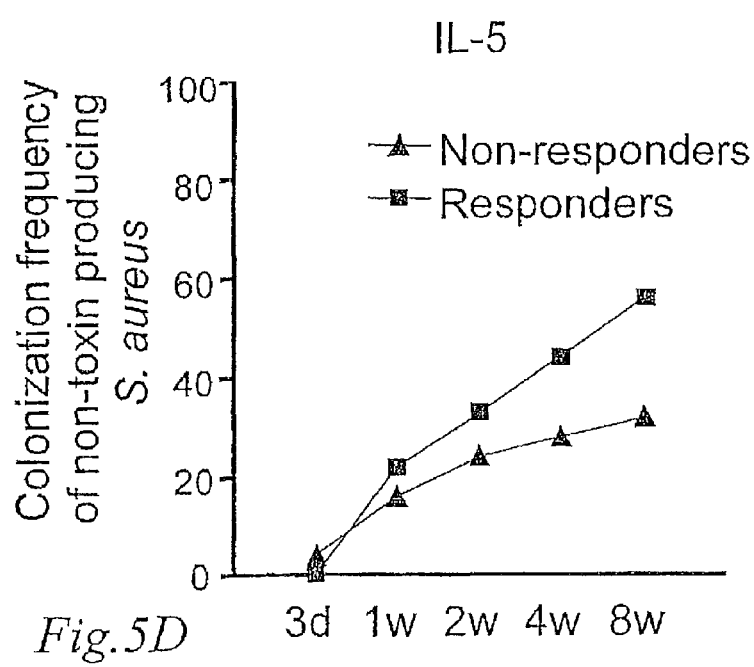
Figure 5E:
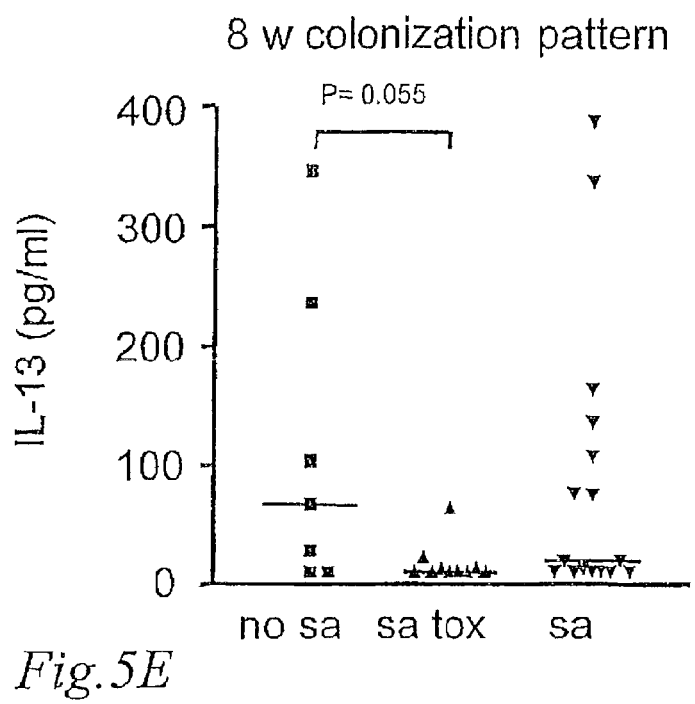
Figure 5F:
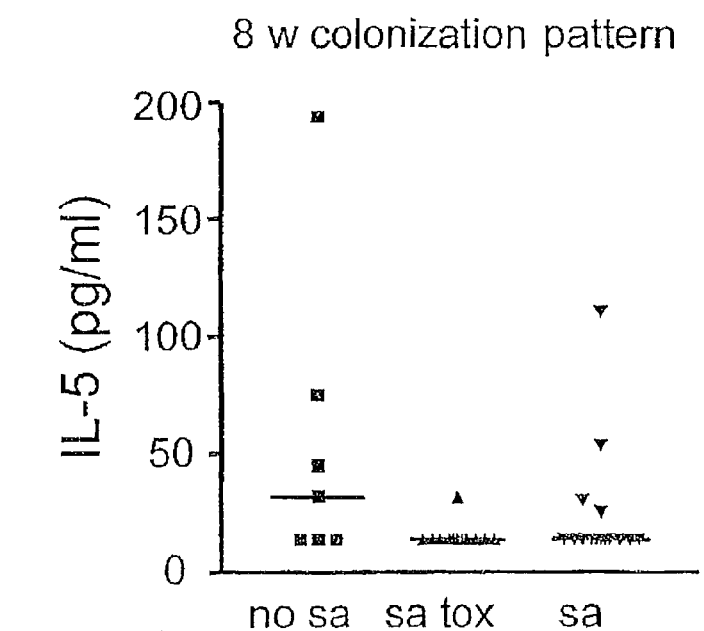

Colonization with Toxin-Producing *S. aureus* Prevents Th2-Responses to Birch Allergen The relation of colonization of toxin-producing *S. aureus* and biological phenomena that could predict hypersensitivity development was examined. Mononuclear cells from blood, collected at 4 months of age, were stimulated in vitro with birch allergen extract and analysed for cytokine production. It was observed that the children who responded (responders) with measurable production of IL-13 and IL-5 (level of detection 11 pg/ml and 14 pg/ml, respectively) were less often colonized with toxin-producing *S. aureus* than the children whose cells produced no IL-13 or IL-5 (non-responders) in response to birch allergen stimulation (FIGS. 5A and 5B). On the other hand, birch allergen reactive children were no less often colonized by non-toxin producing *S. aureus* (FIGS. 5C and 5D). The statistical significance refers to the difference in colonization frequency of toxin-producing *S. aureus* between the responders and non-responders, *P<0.05 (Fisher's exact test). Production of IFN-y and IL-10 in response to birch allergen stimulation was unrelated to *S. aureus* colonization pattern (data not shown). As shown in FIGS. 5E and 5F, birch allergen stimulation induced IL$^L$13 and IL-5 production in cells in only two (16%) and one (8%) infants, respectively, who were colonized with toxin-producing *S. aureus* at 8 weeks of life (sa tox). In contrast, cells from about 60% of the infants who had not been colonized with *S. aureus* (no sa) produced these Th2 cytokines after birch allergen stimulation. Blood cells obtained at the age of 4 months from human infants who were colonized by toxin-producing *S. aureus* in the first few weeks of life respond with less production of IL-5 and IL-13 than other infants in response to stimulation with birch pollen antigen, including those who are colonized by non-toxin-producing *S. aureus* (sa) at the same site. This suggests that they may have lesser risk of developing hypersensitivity and hay fever to birch pollen later in life. Horizontal bars indicate median cytokine production.

Example 6

Colonization with *S. aureus* Down-Regulates Integrin Expression on T-cell

The effect of colonization on T-tell subsets that could be effector cells in inflammatory disease was determined. It has been suggested that expression of the adhesion receptor VLA-4 composed of the proteins CD29 and CD49d is involved in lymphocyte extravasation in several inflammatory and autoimmune diseases. For example, administration of antibodies to VLA-4 is able to abrogate autoimmune diabetes in animal models. The expression of CD29 in both CD4$^+$ and CDEr T-cells in comparison to the children who were colonized with *S. aureus* at the different time points with those who were not colonized with *S. aureus* at any time during the first 8 weeks of life, was analyzed. In FIG. 4G the ratio (4 months/cord blood) of the fraction of 81-integrin$^+$ cells in the CD4$^+$ (A) and CD8$^+$ (B) T-cell populations as a function of colonization of by *S. aureus* at different ages. The statistical significance refers to the difference between the children with intestinal colonization with *S. aureus* at the various time points and the children who were not colonized with *S. aureus* at any time during the first 8 weeks of life (No), *P<0.05 and **P<0.01 (Mann-Whitney U test).

Figure 6A:
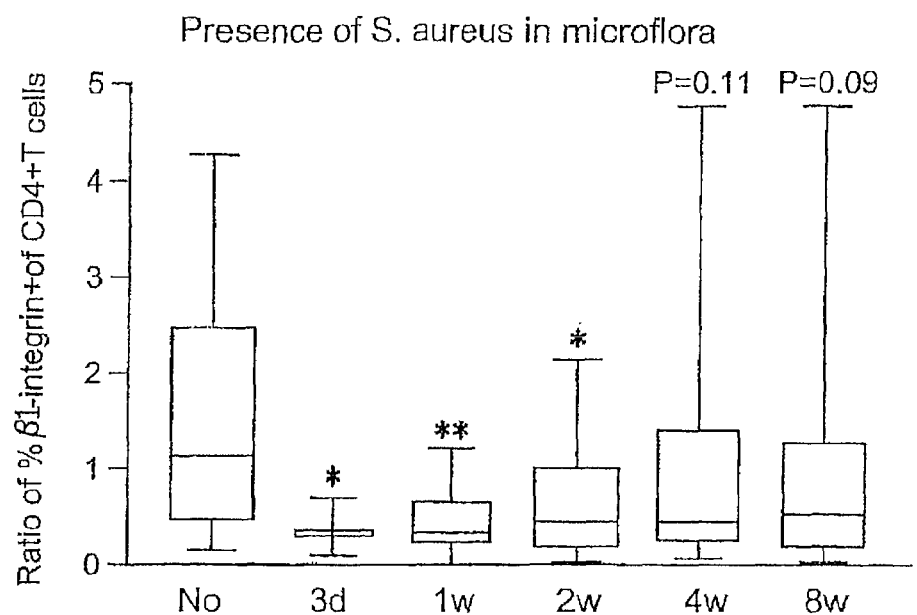
FIGS. 6 A-B show the effect of early S. aureus colonization on T-cell subsets which could be effector cells in inflammatory disease.
Figure 6B:
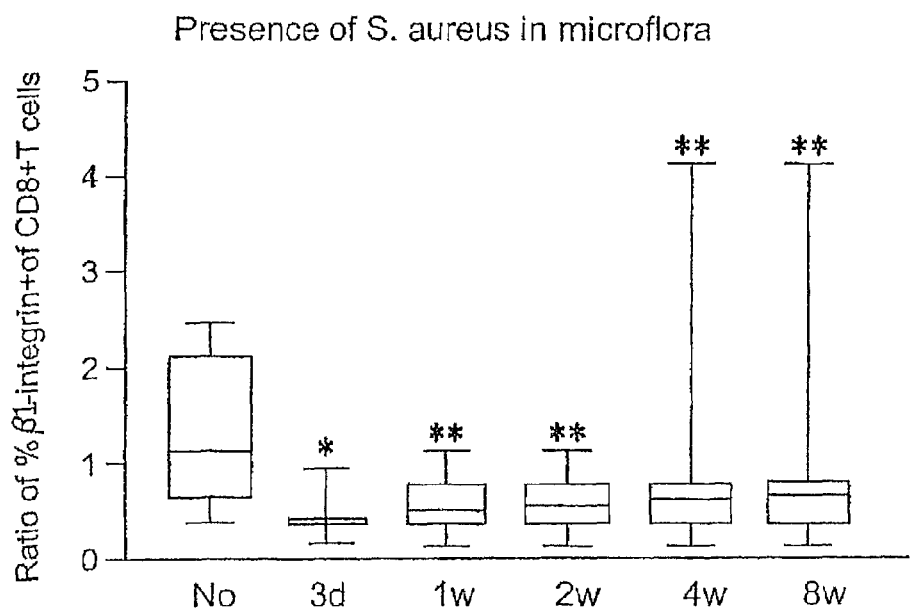

As shown in FIGS. 6A and 6B, the children who were colonized by *S. aureus* had a decreased expression of CD29 on both CD4$^+$ and CD8$^+$ T-cells relative to children without *S. aureus* colonization. To conclude, early colonization with toxin-producing *S. aureus* might prevent induction of Th2-responses to environmental allergens and down-regulate adhesion receptor expression on T-cells.

Example 7

Figure 7:
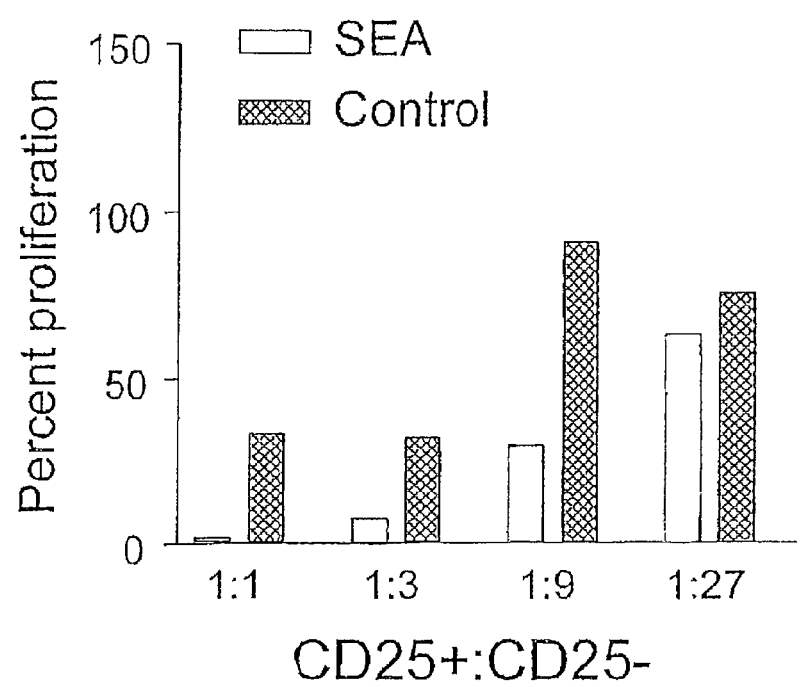
FIG. 7 shows mucosal exposure with superantigen SEA in mice induce functional activity of regulatory T-cells FIGS. 8 A-C show the protective ability of early colonization with S. aureus against gastrointestinal allergic manifestations.

Increased Suppressive Ability of CD25$^+$ Treg from Mice Treated with Mucosal SEA Balb/c mice were given SEA or saline as a control perorally (p.o.) starting at 4 days of age. The treated mice received six doses of 5 microgram SEA/dose every second to third day. At six weeks of age, mice were sacrificed and single cell suspensions were prepared from mesenteric lymph nodes (MLN). For analysis of functional activity of putative Tregs, $CD4^+CD25^+$ and $CD4^+CD25^-$ T-cells were separated using magnetic beads coated with anti-CD25 (MACS system). $CD4^+CD25^+$ and $CD4+CD25^-$ T cells were cultured at different ratios for five days in the presence of the polyclonal T-cell mitogen ConA (FIG. 7). Proliferation was measured as incorporation of 3H-thymidine_ The bars show percent proliferation in co-cultured $CD25^+$ and $CD25^-$ cells at different ratios compared with the corresponding $CD25^-$ cells alone.

It can be seen in FIG. 7 that when infant mice are given superantigens in a liquid solution perorally, the $CD25^+$ putative regulatory T-cells obtain an enhanced capacity to suppress the proliferation of $CD25^-$ T-cells compared to $CD25^+$ putative regulatory cells from untreated mice. This indicates that exposure of the mucosa to superantigen induces a functional activation of the regulatory T-cells which control T-cell activation and inflammatory reactions. Although regulatory T-cells are present in normal mice their functional activity is considerably lower than in mice treated with superantigens. Thus, mucosal exposure with superantigens in infants may prevent induction of inflammatory disorders and immune hyper-reactivity.

Example 8

Figure 8A:
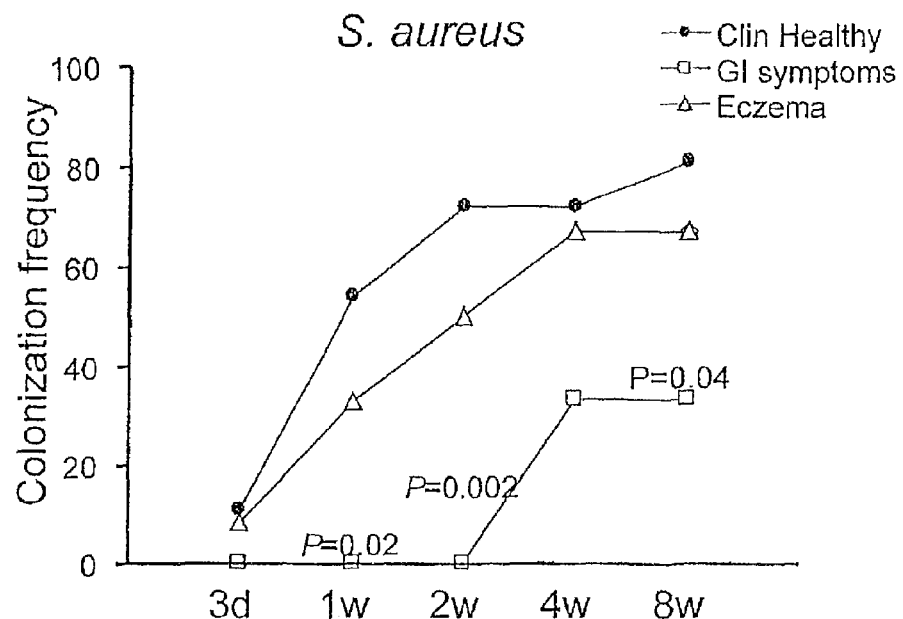
Figure 8B:
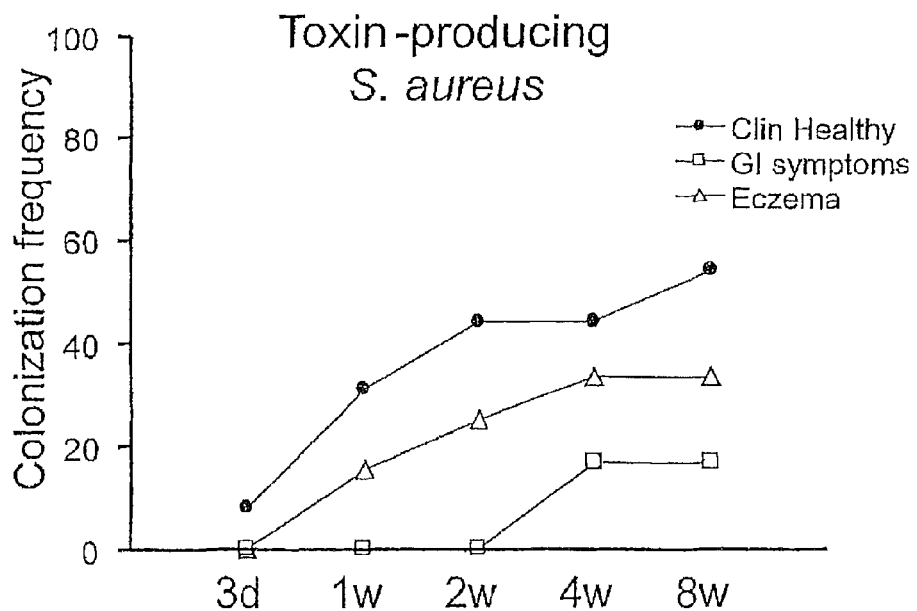
Figure 8C:
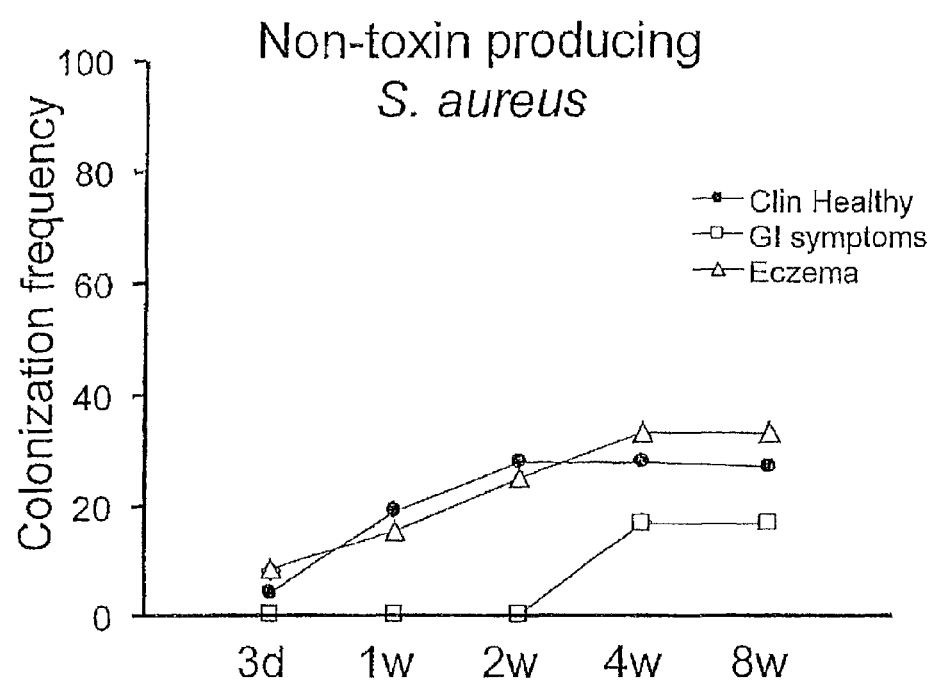

Protective Ability of Early Colonization with S. aureus Against Development of Gastrointestinal Allergic Manifestations in 18-Month Old Children The 64 children were grouped according to development of gastrointestinal allergy or eczema or no allergic disease at 18 months, diagnosed by a pediatric allergologist. The frequency of intestinal colonization with S. aureus in children in these three groups at the ages 3 days, and 1, 2, 4 and 8 weeks had been determined earlier. As can be seen in FIG. 8 A, children with gastrointestinal allergy at the age of 18 months had had significantly lower colonization frequency with S. aureus from 3 days to 8 weeks. No significant difference in colonization frequency was found when children with eczema were compared with healthy children. When S. aureus was divided in toxin-producing (FIG. 8 B) and non-toxin producing strains (FIG. 8 C), a similar trend was seen in particular for the toxin-producing strains but because of too low numbers of children in the groups, statistical significance was not obtained.

Children who developed gastrointestinal allergy before 18 months acquired S. aureus later that children who remained healthy or who developed eczema. However a trend for lower colonization frequency with toxin-producing strains was also seen in the children with eczema. Eczema is known to be less predictive for later development of atopic allergy than gastrointestinal allergy, in that 60% of the children with eczema later develop, positive skin prick test, asthma and hay fever. Thus, early S. aureus colonization stands a good chance of preventing allergy at a later age, which has to be proven by following the children prospectively. To obtain a significant difference with the toxin-producing strains regarding allergy development a new study is needed in which children with toxin-producing strains are selected in order to increase the number of children in that group.

Pharmaceutical Compositions

The strains, toxins and the superantigen(-s) of the present invention may be isolated in any level of purity by standard methods and purification can be achieved by conventional means known to those skilled in the art, such as distillation, recrystallization and chromatography.

The strains, toxins and the superantigen(-s) of the invention may be administered alone or in combination with pharmaceutically acceptable carriers or diluents, and such administration may be carried out in single or multiple doses.

Compositions may, for example, be in the form of tablets, pills sachets, vials, hard or soft capsules, aqueous or oily suspensions, aqueous or oily solutions, emulsions, powders, granules, syrups, elixirs, lozenges, reconstitutable powders, liquid preparations, sprays, creams, salves, jellies, gels, pastes, ointments, liquid aerosols, dry powder formulations, or HFA aerosols.

The compositions of the invention may be in a form suitable for administration through oral, buccal routes, or for administration by inhalation or insufflation (e.g. nasal, tracheal, bronchial) routes.

Depending upon the disorder and patient to be treated and the route of administration, the compositions may be administered at varying doses.

Oral, Buccal or Sublingual

For oral, buccal or sublingual administration, the compounds of the present invention may be combined with various excipients. Solid pharmaceutical preparations for oral administration often include binding agents (for example syrups and sugars, acacia, gelatin, sorbitol, tragacanth, polyvinylpyrrolidone, sodium lauryl sulphate, pregelatinized maize starch, hydroxypropyl methylcellulose, lactose, starches, modified starches, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone and sodium alginate), disintegrants (such as starch and preferably corn, potato or tapioca starch, alginic acid and certain complex silicates, polyvinylpyrrolidone, sucrose, gelatin, acacia, sodium starch glycollate, microcrystalline cellulose, crosscarmellose sodium, crospovidone, hydroxypropyl methylcellulose and hydroxypropyl cellulose), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols and sodium stearyl fumarate) and fillers (including high molecular weight polyethylene glycols, lactose, sugar, calcium phosphate, sorbitol, glycine magnesium stearate, starch, glucose, lactose, sucrose, rice flotir, chalk, gelatin, microcrystalline cellulose, calcium sulphate, xylitol and lactitol). Such preparations may also include preservative agents and anti-oxidants.

Liquid compositions for oral administration may be in the form oft for example, emulsions, syrups, or elixirs, or may be presented as a dry product for reconstitution with water or other suitable vehicle before use. Such liquid compositions may contain conventional additives such as suspending agents (e.g. sorbitol, syrup, methyl cellulose, hydrogenated edible fats, gelatin, hydroxyalkylcelluloses, carboxymethylcellulose, aluminium stearate gel, hydrogenated edible fats) emulsifying agents (e.g. lecithin, sorbitan monooleate, or acacia), aqueous or non-aqueous vehicles (including edible oils, e.g. almond oil, fractionated coconut oil) oily esters (for example esters of glycerine, propylene glycol, polyethylene glycol or ethyl alcohol), glycerine, water or normal saline; preservatives (e.g. methyl or propyl p-hydroxybenzoate or sorbic acid) and conventional flavoring, preservative, sweetening or colouring agents. Diluents such as water, ethanol, propylene glycol, glycerin and combinations thereof may also be included.

Other suitable fillers, binders, disintegrants, lubricants and additional excipients are well known to a person skilled in the art.

Nasal/Inhalation

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluorormethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve which delivers a measured amount of active compound.

Materials and Methods

Infants

Sixty-four healthy Swedish infants born in 2001-2003 at the Sahlgrenska University Hospital (Goteborg, Sweden) were included in the study. These children formed part of a prospective birth-cohort study aiming to investigate the relation between intestinal colonization pattern in infancy and development of the immune system. Informed consent was obtained from the parents and the study was approved by the Human Research Ethics Committee of the Medical Faculty, GOteborg University, Sweden. Cord blood was obtained from 53 children and peripheral blood samples from 61 children at 4 months of age (6 ml). The blood was collected in heparinized tubes.

Flow Cytometry

Phenotypic analysis of lymphocytes in Whole blood was performed by flow cytometry within 48 h of collection. The following anti-human monoclonal antibodies were used: APC-conjugated anti-CD3 (SK7) and anti-CD29 (MAR4); FITC-conjugated anti-CD4 (SK3) and anti-CD25 (2A3); PerCP-conjugated anti-CD8 (SKI); biotinylated anti-CTLA-4 (BNI3). All antibodies and streptavidin-PE were purchased from Becton-Dickinson (Erembodegum, Belgium). For surface staining, whole blood (100 pl per tube) was incubated with antibodies for 20 min at 4° C. in the dark, 2 ml of FACS lysing solution (Becton Dickinson) was added, followed by incubation for another 15 min. When performing intracellular staining for CTLA-4, cell-surface staining of CD25 and CD4 was first completed before the cells were permeabilized using a Cytofix/Cytoperm Kit (Pharmingen, San Diego, Calif.). To block non-specific staining of permeabilized cells, biotinylated anti-CTLA-4, isotype control antibody and streptavidin-PE were diluted in Perm/Wash solution containing 1% AB-serum. Analysis was performed on a FacsCalibur (Becton-Dickinson) equipped with CellQuest software and 5000 lymphocytes were recorded.

TruCOUNT Assay

The TruCOUNT assay was used to determine the absolute count of various subsets of lymphocytes in blood (Becton Dickinson). Fifty pl of undiluted whole blood was stained with PerCP-conjugated anti-CD45 antibodies in TruCOUNT tubes. After 15 min at room temperature in the dark, 450 pl of lyzing solution was added, followed by incubation for 15 min. The samples were then analysed with flow cytometry. In a dot plot of CD45-PerCP versus SSC, the lymphocytes were defined on the characteristics of low SSC and high CD45 and gated accordingly. A further dot plot was created to identify the beads using a FL1 versus FL2 plot. The beads were defined as having high FL1 and high FL2 properties. The absolute cell count for lymphocytes was calculated using the following formula: events of lymphocytes/events of beads× number of beads per TruCOUNT tube/blood volume.

Cell Cultures

Peripheral blood mononuclear cells (PBMC) were isolated from whole blood by density gradient centrifugation over Lymphoprep™ (Nycomed, Oslo, Norway) for 20 min (900 g, room temperature) within 5 hours of collection. The cells were washed three times in PBS and were adjusted to $10^6$ per ml in serum-free AIM-V medium (Invitrogen, San Diego, Calif.) containing L-glutamine, 50 pg streptomycin sulfate per ml, 10 pg gentamicin sulfate per ml and 20 pM mercaptoethanol. The mononuclear cells were transferred to 96-well plates and stimulated with 50 pg birch allergen extract per ml (Greer Laboratories, Lenoir, USA) for 6 days at 37° C. with 5% $CO_2$.

Cytokine Determination

A standard ELISA protocol was preformed as describes elsewhere (Karlsson, H., Hessle, C. & Rudin, A. Innate immune responses of human neonatal cells to bacteria from the normal gastrointestinal flora. *Infect Immun* 70, 6688-96, 2002) All antibodies purified proteins were purchased from BD Pharmingen, San Diego, Calif. Costar plates (Invitrogen, San Diego, Calif.) were coated with the following anti-human capture mAb: IL-13 (JES10-5A2), IL-5 (TRFK5), IFN-y (NIB42) and IL-10 (JES3-9D7). Standard curves were generated using recombinant human IL-13, IL-5, IFN-y and IL-10, respectively. The following biotinylated mAb were used: IL-13 (B69-2), IL-5 (JES1-5A10), IFN-y (4S.B3) and IL-10 (JES3-12G8). Samples, standard curves, biotinylated antibodies and streptavidin-horseradish peroxidase were diluted in high performance ELISA dilution buffer (Sanquin, Amsterdam, The Netherlands).

Sampling of the Intestinal Microflora

A sample of the rectal flora was obtained 3 days after delivery using a cotton-tipped swab. Faecal samples were obtained at 1, 2, 4 and 8 weeks and at 6 and 12 months of age and kept under anaerobic conditions until they were processed within 24 h after collection. Rectal swab samples were cultured on selective and non-selective media for the isolation of aerobic or facultatively anaerobic bacteria. The inoculate was spread to obtain free-lying colonies. Faeces were serially diluted in sterile peptone water, and appropriate dilutions were plated on selective and non-selective media and incubated under aerobic or anaerobic conditions for the isolation aerobic or facultatively anaerobic bacteria and anaerobic bacteria, respectively.

Bacterial Identification

Enterobacteria and enterococci were isolated from Drigalski and enterococcosel agar, respectively, and identified as previously described (Adlerberth et al in manuscript 2004). Staphylococci were quantified on staphylococcus agar, and defined by their typical Gram-stained appearance and a positive catalase reaction. Coagulase-positive staphylococci were identified as *S. aureus*, while other staphylococci were defined as coagulase-negative (CoNS). One isolate of each *S. aureus* strain was cultivated overnight in broth and tested for toxin-production by reversed passive latex agglutination. The SET-RPLA kit was used to detect enterotoxin A, B, C and D and the TST-RPLA kit for TSST-1 (both from Oxoid, Hampshire, Great Britain). Anaerobic bacteria belonging to the genera *Bacteroides, Bifidobacterium, Lactobacillus* or *Clostridium* were isolated from anaerobic cultures on *Bacteroides* Bile Esculine, Beerens, Rogosa and *Brucella* or CCFA agar, respectively, and identified to the genus or species level as previously described (Adlerberth et al in manuscript 2004).

Assessment of Signs and Symptoms of Allergy

All children were examined by 18 months of age by a paediatric allergologist. A structured interview was performed with recording of gastro-intestinal, respiratory and skin signs and symptoms of allergy.

Statistical Analysis

All statistical analyses were performed using GraphPad Prism. Fisher's exact test was used to compare *S. aureus* colonization frequency in different groups of children on the basis of various parameters as indicated in the corresponding figure legends. Mann-Whitney U test was used to compare expansion of different T-cell subset as a function of *S. aureus* colonization at different ages and to compare levels of cytokine production from PBMC from children with different colonization patterns. Paired t-test was used to analyze the difference in T-cell subsets in cord blood and in peripheral blood at 4 months of age.

What is now claimed:

1. A method for reducing the incidence of an allergic disorder, the method comprising:
   administering a pharmaceutical composition onto a mucous membrane in a newborn human infant, wherein
   the pharmaceutical composition comprises a therapeutically effective dose of (i) at least one isolated *Staphylococcus aureus* superantigen or (ii) isolated *Staphylococcus aureus* bacteria,
   the pharmaceutical composition is administered to a newborn infant within 3 months after birth when it comprises isolated-*Staphylococcus aureus* superantigens, and
   the pharmaceutical composition is administered to a newborn infant within one week after birth when it comprises isolated *Staphylococcus aureus* bacteria.

2. The method according to claim 1, wherein the isolated *Staphylococcus aureus* bacteria are an enterotoxin producing strain of *Staphylococcus aureus*.

3. The method according to claim 1, wherein the isolated *Staphylococcus aureus* superantigen is selected from the group consisting of enterotoxins A, B, C, D, E, or TSST-1.

4. The method according to claim 1, wherein the isolated *Staphylococcus aureus* superantigen is *Staphylococcus aureus* enterotoxin A.

5. The method according to claim 1, wherein the mucous membrane is the intestinal mucous membrane.

6. The method according to claim 1, wherein the mucous membrane is the nasal mucous membrane.

7. The method according to claim 5, wherein the pharmaceutical composition is administered to a newborn human infant within one week after birth.

8. The method according to claim 5, wherein the pharmaceutical composition is administered to a newborn human infant within 6 days after birth.

9. The method according to claim 5, wherein the pharmaceutical composition is administered to a newborn human infant within 5 days after birth.

10. The method according to claim 5, wherein the pharmaceutical composition is administered to a newborn human infant within 4 days after birth.

11. The method according to claim 5, wherein the pharmaceutical composition is administered to a newborn human infant within 3 days after birth.

12. The method according to claim 1, wherein the pharmaceutical composition is generating regulatory T-cells in vivo.

13. The method according to claim 1, wherein the pharmaceutical composition is generating CD25+ regulatory T-cells in vivo.

14. The method according to claim 1, wherein the allergic disorder is an allergy.

* * * * *